United States Patent [19]

Levine

[11] Patent Number: 4,746,238
[45] Date of Patent: May 24, 1988

[54] STICK SWAB WITH AUGURED HEAD

[76] Inventor: Robert A. Levine, 31 Pilgrim La., Guilford, Conn. 06437

[21] Appl. No.: 925,979

[22] Filed: Nov. 3, 1986

[51] Int. Cl.⁴ .......................................... B05C 21/00
[52] U.S. Cl. .................................................. 401/196
[58] Field of Search ............... 401/196; 132/88.5, 88.7

[56] References Cited

U.S. PATENT DOCUMENTS 3,324,855 6/1967 Heimlich .............................. 401/196
4,329,990 5/1982 Sneider ................................. 401/196

FOREIGN PATENT DOCUMENTS 89271 9/1983 European Pat. Off. ................ 604/1
811756 4/1959 United Kingdom .................... 604/1

Primary Examiner—Gregory E. McNeill
Attorney, Agent, or Firm—William W. Jones

[57] ABSTRACT

The stick swab has one or more compliant heads adapted for cleaning body orifices such as ear canals. The head or heads are formed with a contoured outer surface to aid in gripping and removing material or debris from the body orifices. The contours preferably take the form of a helical augur whereby material will be withdrawn from the orifice merely by appropriately rotating the swab about its axis.

7 Claims, 1 Drawing Sheet

STICK SWAB WITH AUGURED HEAD

This invention relates to an improved swab stick of the type having enlarged fibrous or compliant head disposed at one or both ends of the stick. More particularly, this invention relates to a swab stick which has a positive material gripping feature on the fibrous heads to provide improved adherance of material to the fibrous heads whereby material and/or debris can be cleaned out of body orifices with an auguring action.

Cotton fiber swabs on the ends of sticks are well known in the prior art. These swabs will include a wooden, cardboard or plastic stick portion with fibrous enlarged cotton swab heads affixed to both ends of the stick portion. The swabs are used for many purposes, a primary one of which is for cleaning wax and other material out of the ears. The prior art stick swabs rely on the fibrosity of the heads to ensnare the material being removed. Thus, the swab heads must be relatively firmly pressed against the tissue which is being cleaned to be effective. This can result in harm to fragile tissues such as are found in the ear canal, or the like, and can also result in material or debris being pushed further into the ear canal.

This invention relates to a swab stick of the general character described above wherein the fibrous head or heads are contoured to improve their ability to ensnare material without requiring the use of undue pressure against the tissues being cleaned. The swabs of this invention are provided with generally circumferential ridges on their heads so as to increase their ability to ensnare or entrain the material which is being removed by the swab. The ridges are preferably helical in configuration so that they will act as an auger when the swab is rotated in the appropriate direction about its axis. The ridges will form a left hand helix on the head at one end of the swab stick, and a right hand helix on the opposite end of the stick. There will be imprinted on the stick indicia, such as one or more arrows, which will identify the proper direction of rotation of the stick. The ridges can be formed by a separate component, such as a string, which is appropriately wrapped about the fibrous head. The ridges can also be formed by a localized modification of the hardness of the fibrous head. Such a modification can be accomplished by impregnating the fiber with an additive which renders the fibers selectively hardenable. Such an additive could be starch, for example. Alternatively, the modification can be accomplished by using an artificial compliant material which can be locally altered, for example, by application of heat. Typically such artificial materials could be a urethane polymer or the like. Another way of forming the ridges would be to form the stick of injection molded plastic and form the ridges on the ends of the stick which underlie the fibrous swabs. The fiber would be deposited evenly over the ridged ends of the stick and would assume the shape of the ridged ends.

It is therefore an object of this invention to provide an improved swab stick having contoured swabs which provide increased ability to ensnare or capture material without the need of applying excessive pressure to tissues being cleaned with the swabs.

It is an additional object of this invention to provide a swab of the character described having a helical rib on the fibrous ends thereof which rib is operable to clean material from tissue in an auger-like fashion by rotating the swab stick about its axis.

It is another object of this invention to provide a swab of the character described wherein the helical ribs on opposite ends of the stick are pitched in opposite directions so that either can be used in auger fashion by unidirectional rotation of the stick.

These and other objects and advantages of the invention will become more readily apparent from the following detailed description of several preferred embodiments of the invention when taken in conjunction with the accompanying drawings, in which.

Figure 1:
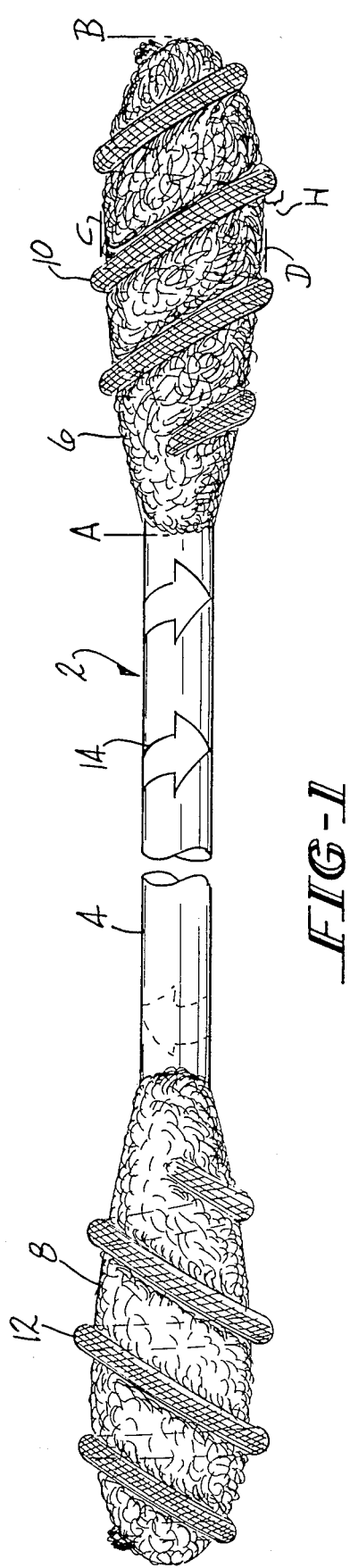
FIG. 1 is a fragmental side elevational view of one embodiment of a swab formed in accordance with this invention.

Referring now to the drawings, the swab, denoted generally by the numeral 2, has a stick portion 4 having the tufted fibrous heads 6 and 8 mounted at each end. Each fibrous head has a helical rib 10 and 12 formed thereon. In the FIG. 1 embodiment, the ribs 10 and 12 are formed by a filament which is coiled about the heads 6 and 8 and adhered thereto. It will be noted that one rib is left hand helix and the other is a right hand helix. Arrow indicia 14 are imprinted on the stick 4 to indicate the proper direction that the swab should be rotated when used. The helix can have from one to four ribs over the length of each head 6 and 8. The length of each head should be between one and two centimeters as measured between A and B. The major thickness of the heads as measured between C and D must be between 2 and 4 millimeters. The ribs will have a height H of 1 to 2 millimeters.

Figure 3:
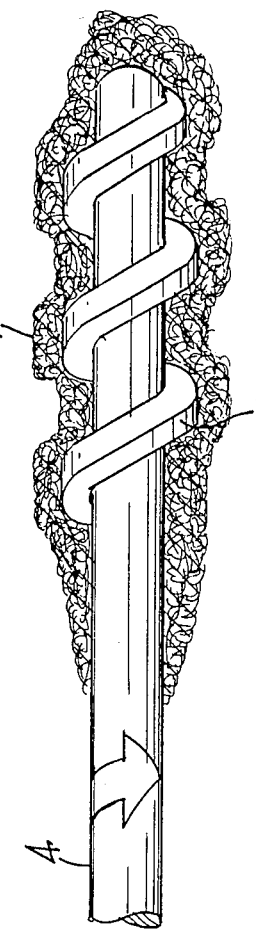
FIG. 3 is a view similar to FIGS. 1 and 2 but showing still another embodiment of the swab of this invention having a polygonal shaped rib.
Figure 2:
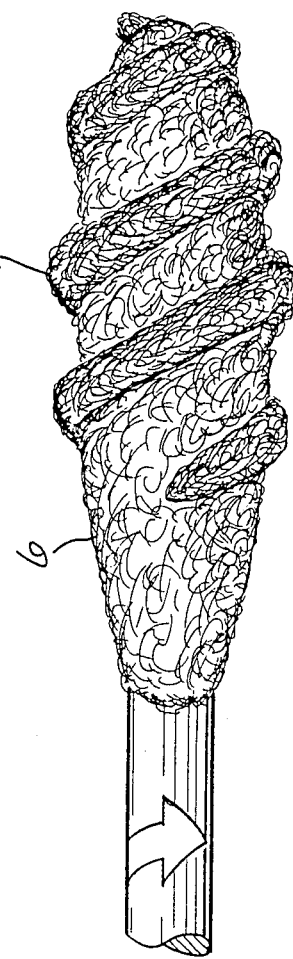
FIG. 2 is a view similar to FIG. 1 but showing one end of another embodiment of a swab formed in accordance with this invention.
Figure 4:
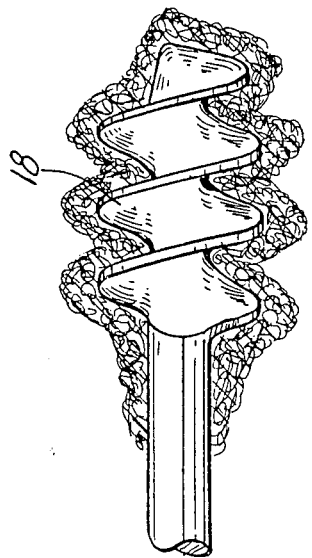
FIG. 4 shows an embodiment similar to that shown in FIG. 3 wherein the underlying portions of the stick are twisted to form the ribs.

As shown in FIG. 2, the ribs 10 can be formed by local deformation and hardening of the fibrous material forming the heads 6 and 8, and as shown in FIG. 3, the ribs 16 can be formed with a polygonal shape i.e. rectangular by deformation of the underlying portions of the stick. This can be done by injection moulding of the sticks from plastic, for example. Helical ribs 16 are thus formed at the ends of the sticks and the fibrous material is then evenly deposited over the helical ends of the sticks. As shown in FIG. 4 the ribs 18 can be formed by flattening the ends of the stick and then twisting the flattened end to form the helix. The sticks can be formed from extruded plastic in this embodiment.

It will be appreciated that the swab of this invention will display an improved ability to capture material or debris to be cleaned from body orifices, as for example wax material from the ear canal. The simple rotational movement of the swab provides positive displacement of material engaged by the ribs. The swabs are easy to manufacture and provide improved performance. The heads may be fibrous or may be made from a non-fibrous compliant material.

Since many changes and variations of the disclosed embodiments may be made without departing from the inventive concept, it is not intended to limit the invention otherwise than as required by the appended claims.

What is claimed is:

1. A stick swab for cleaning bodily orifices such as the ear, and comprising: a stick portion; means forming elongated swab heads on each end of said stick portion, one of said swab heads having an enlarged helical ribe with a left hand spiral, and the other of said swab heads having an enlarged helical rib with a right hand spiral when said stick swab is viewed in elevation; and means visible on said stick portion for indicating a direction for rotating said stick swab about its axis, which direction will cause both of said swab head ribs to augur material out of the orifice when said swab heads are inserted into the orifice.

2. The stick swab of claim 2 wherein said swab heads are formed from an artificial material, and said ribs are formed by locally altering the hardness of said artificial material so that the ribs are harder than the remainder of the swab heads.

3. The stick swab of claim 2 wherein said artificial material is urethane polymer.

4. The stick swab of claim 1 wherein said swab heads are formed from a fibrous material which is impregnated with an additive which renders the fibers selectively hardenable at said ribs.

5. The stick swab of claim 4 wherein said additive is starch.

6. The stick swab of claim 1 wherein there are helixes formed on end portions of said stick portion, and said swab heads are formed from pliant material overlying said helixes with said pliant material bieng of substantially constant thickness over said helixes whereby said pliant material assumes the configuration of said helixes to form said helical ribs.

7. The stick swab of claim 1 wherein said helical ribs are formed from a filament helically wound about said swab heads.

* * * * *